United States Patent
Holmström et al.

[11] Patent Number: 5,935,158
[45] Date of Patent: Aug. 10, 1999

[54] ELECTRODE LEAD AND DEVICE FOR TISSUE STIMULATION AND/OR DETECTION OF TISSUE RESPONSE

[75] Inventors: Nils Holmström, Järfalla; Sven-Erik Hedberg, Kungsängen; Kenth Nilsson, Akersberga, all of Sweden

[73] Assignee: Pacesetter AB, Järfälla, Sweden

[21] Appl. No.: 08/915,756

[22] Filed: Aug. 21, 1997

[30] Foreign Application Priority Data

Aug. 23, 1996 [SE] Sweden .................................. 9603066

[51] Int. Cl.⁶ .............................. A61N 1/04; A61N 1/05
[52] U.S. Cl. ............................................ 607/116; 607/123
[58] Field of Search ................................. 607/116, 122, 607/123, 126, 127

[56] References Cited

U.S. PATENT DOCUMENTS

| | | |
|---|---|---|
| 4,485,813 | 12/1984 | Anderson et al. . |
| 4,798,206 | 1/1989 | Maddison et al. ...................... 607/122 |
| 5,109,842 | 5/1992 | Adinolfi . |
| 5,304,208 | 4/1994 | Inguaggiato et al. . |
| 5,324,326 | 6/1994 | Lubin . |
| 5,423,883 | 6/1995 | Helland . |
| 5,433,731 | 7/1995 | Hoegnelid et al. . |
| 5,496,361 | 3/1996 | Moberg et al. . |
| 5,514,171 | 5/1996 | Hoegnelid et al. . |
| 5,800,536 | 9/1998 | Fisher et al. . |

FOREIGN PATENT DOCUMENTS 0 473 070   3/1992   European Pat. Off. .

*Primary Examiner*—William E. Kamm
*Assistant Examiner*—Carl H. Layno
*Attorney, Agent, or Firm*—Hill & Simpson

[57] ABSTRACT

An implantable electrode for stimulating tissue has a piezo-electric electrode for electrically and mechanically stimulating tissue and for detecting electrical and mechanical evoked response of the stimulated tissue. An implantable lead and an implantable stimulation device employing such an electrode are described including diagnostic circuitry for making a diagnosis of the heart condition using such an electrode.

25 Claims, 2 Drawing Sheets

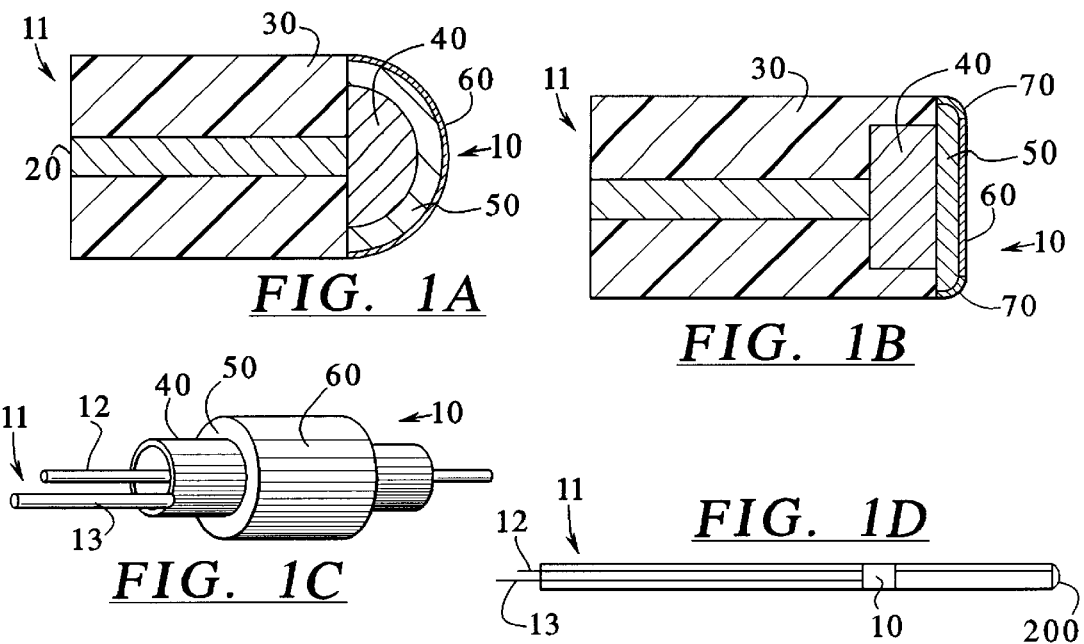
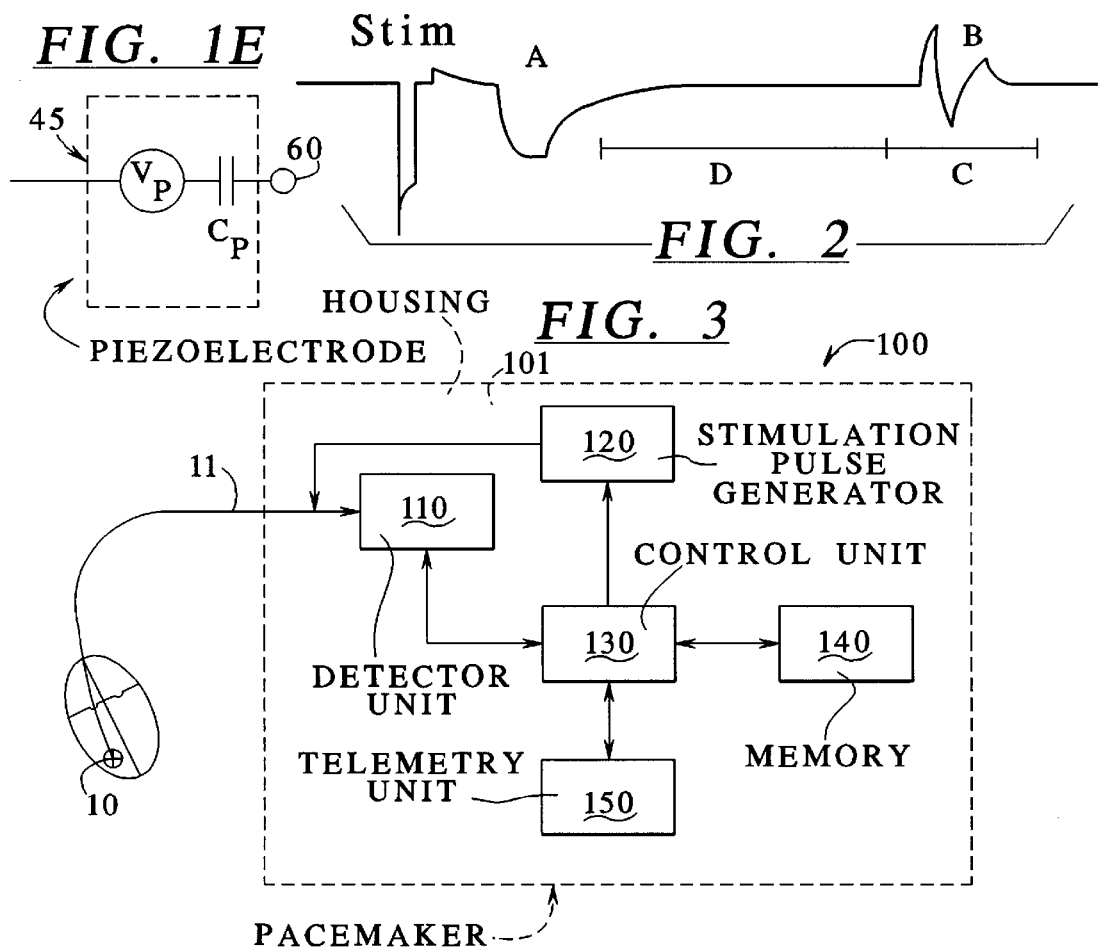

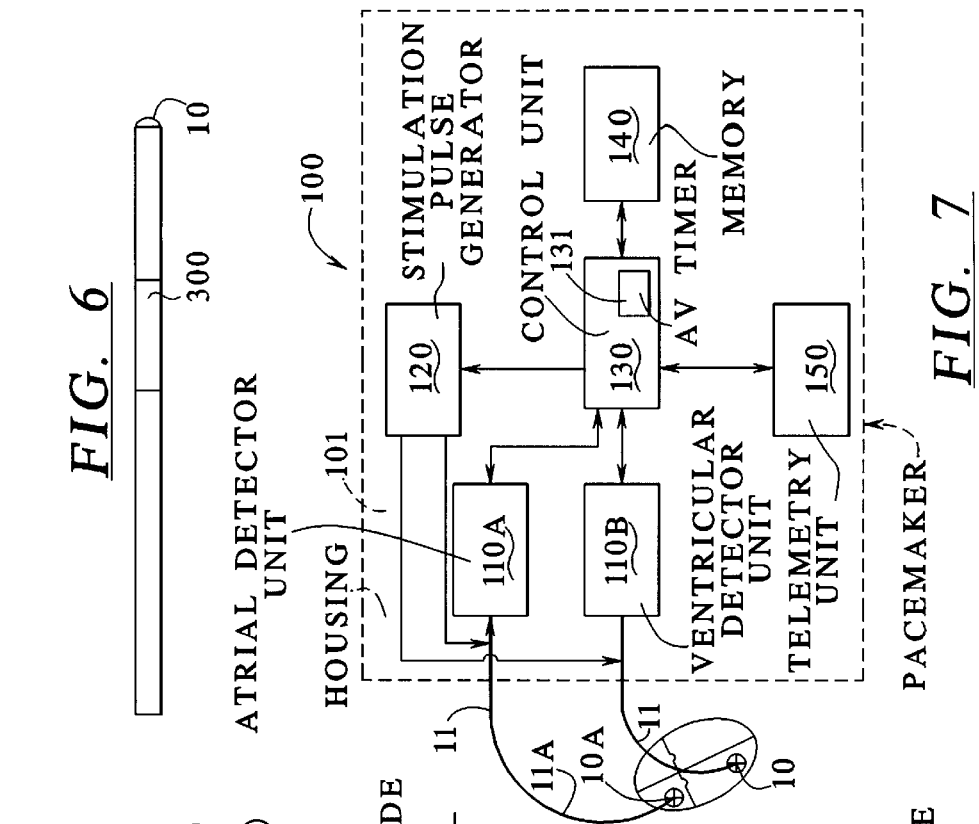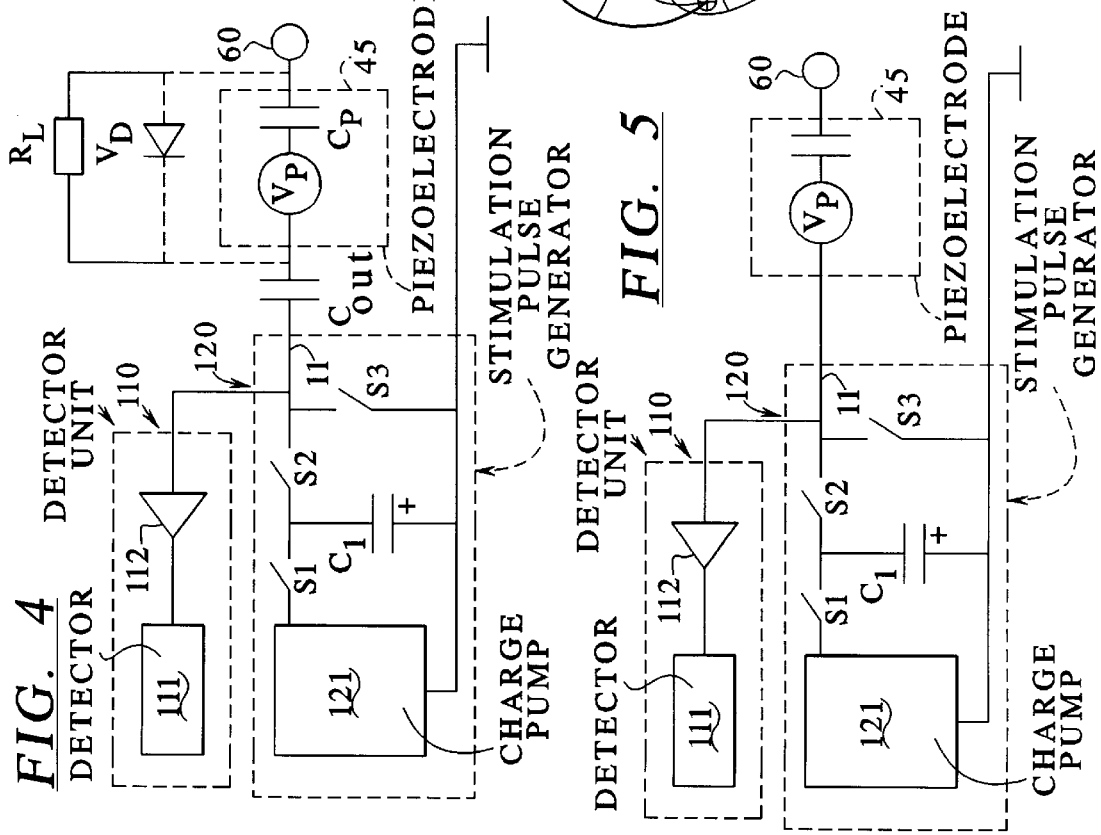

ELECTRODE LEAD AND DEVICE FOR TISSUE STIMULATION AND/OR DETECTION OF TISSUE RESPONSE

FIELD OF THE INVENTION

The invention relates generally to an electrode for implantable stimulation devices such as heart pacemakers or defibrillators. The invention relates further to implantable leads and stimulation devices such as heart pacemakers or defibrillators which comprise such an electrode. Moreover, the invention relates to the use of the electrode for diagnosing the condition of stimulated tissue.

DESCRIPTION OF THE PRIOR ART

The life span of most pacemakers is dictated by the rate at which their batteries drain. Thus, a substantial effort has been directed toward minimizing the amount of energy used by pacemakers, while ensuring that the devices continue to deliver effective therapy. For example, demand pacemakers effectively reduce the battery drain by delivering pacing pulses only when required, i.e. if the pacemaker has not detected any spontaneous activity. Another way to reduce the current consumption is to minimize the amplitude and/or the duration of the stimulation pulse to a value just above the capture threshold. There are, however, times when the heart emits an electrical signal, without providing a corresponding mechanical contraction (electromechanical dissociation). The pacemaker detects and interprets the electrical signal as an intrinsic beat or an evoked response. There are also times when the heart does not respond normally with increased cardiac output for increased stimulation rate as, for example, in patients with coronary artery disease during angina pectoris.

A way of minimizing the amount of energy needed for defibrillation, while ensuring that the defibrillators still delivers effective therapy, is disclosed in U.S. Pat. No. 5,433,731 to Högnelid et al. wherein a defibrillator is described having means for supplying the heart with a mechanical shock instead of an electrical shock. One embodiment employs an electrode for supplying a defibrillation pulse, the electrode being provided with an element on its distal exterior, which presses against the heart tissue and converts the electrical energy into mechanical energy. The element can, for example, be a piezoelectric element.

U.S. Pat. No. 5,304,208 to Inguaggiato et al. discloses a cardiostimulator device having an electrode including an acceleration sensor for detecting the acceleration to which the cardiac mass is subjected as a reaction to any contraction whatsoever of the cardiac mass. The acceleration sensor is solely sensitive to inertial forces and can therefore be located in an entirely rigid capsule and consequently can be entirely insensitive to the pressure in the ventricle or the atrium, and to pressure which the cardiac wall can exert, particularly on the distal electrode.

SUMMARY OF THE INVENTION

It is an object of the present invention to provide an implantable medical electrode, an implantable medical lead and an implantable medical device for administering medical therapy to a subject in the form of electrical stimulation pulses, wherein the pulses achieve a comparable therapeutic effect to pulses administered by known electrodes, leads and devices, but which have a reduced electrical energy content.

The above object is achieved in accordance with the principles of the present invention in an implantable medical electrode, an implantable electrode lead, and an implantable stimulation therapy administration and evaluation device wherein stimulation energy is administered, and physiological energy is detected, as a combination of electrical energy and mechanical energy. The stimulation and detection take place via an electrode having a transducer in the form of a piezoelectric element. The transducer operates in both directions, i.e., to convert electrical energies supplied to the transducer into electrical energy and mechanical energy for transfer to surrounding physiological tissue, as well as to transfer (receive) mechanical and electrical energy from the surrounding tissue and to convert the received electrical and mechanical energy into an electrical signal.

An advantage of the invention is that it is possible to more reliably stimulate heart tissue and to detect a heart contraction. As a result a lower energy consumption is ensured.

In a preferred embodiment the piezoelectric electrode is formed by an element of piezoelectric material covered by a conductive layer. In another embodiment the piezoelectric electrode is the tip electrode of the lead and in another embodiment the piezoelectric electrode is the ring electrode. In a preferred embodiment the stimulation pulse generator supplies the electrode with a chopped stimulation pulse.

BRIEF DESCRIPTION OF THE DRAWINGS

FIG. 1A and 1B respectively schematically show two embodiments of a tip electrode in accordance with the invention, for both electrically and mechanically stimulating tissue and detecting an evoked response.

FIG. 1C schematically shows an embodiment of a ring electrode in accordance with the invention, for both electrically and mechanically stimulating tissue and detecting an evoked response.

FIG. 1D schematically shows an electrode lead in accordance with an embodiment of the invention.

FIG. 1E is a schematic equivalent circuit of the piezoelectric electrode in accordance with an embodiment of the invention.

FIG. 2 is a pulse diagram of the detector input signal generated by the electrode in accordance with an embodiment of the invention and including the stimulation pulse, the electrical evoked response and the mechanical evoked response.

FIG. 3 is a block diagram of a heart pacemaker for single chamber pacing incorporating an electrode in accordance with the invention.

FIG. 4 is a block circuit diagram of a heart pacemaker in accordance with a first embodiment of the invention.

FIG. 5 is a block circuit diagram of a heart pacemaker in accordance with a second embodiment of the invention.

FIG. 6 schematically shows a single lead, with a piezoelectric electrode in accordance with an embodiment of the invention at the tip of the lead and an intravascular defibrillation electrode behind the tip.

FIG. 7 is a block diagram of a heart pacemaker for dual chamber pacing incorporating electrodes in accordance with the invention.

DESCRIPTION OF THE PREFERRED EMBODIMENTS

FIGS. 1A and 1B show an electrode 10 for a heart pacemaker 100. The electrode 10 has a conductor 20 enclosed by an insulator 30, e.g. of silicon rubber. The conductor 20 is at one end in contact with an electrically conductive core 40, which is covered with a piezoelectric material 50. In order to obtain a high capacitance, usually of the order 10–100 nF, the layer of piezoelectric material 50 is very thin (0, 1–5 μm). The piezoelectric material 50 is covered with an electrically conductive layer 60. The conductive layer 60 is preferably a high double-layer capacitance toward the tissue for transferring more energy to the tissue without obtaining a voltage drop during the stimulation of the tissue. This technique is well-known to a person of skill in pacemaker technology. The metal core 40, the piezoelectric layer 50 and the conductive layer 60, i.e. the piezoelectric electrode, form the tip of the electrode lead 11.

FIG. 1A and 1B show a hemispherical and a planar embodiment of the tip respectively, the planar embodiment being more sensitive to how it is placed with respect to the myocardial tissue. In a preferred embodiment the conductor 20 is made of the commonly used alloy MP35 and the conductive core 40 of e.g. graphite, titanium, platinum or iridium. The conductive layer 60 is preferably porous for increasing the contact area between the electrode and the tissue to be stimulated and it is furthermore biocompatible, e.g. vitreous carbon, porous titanium nitride, porous titanium carbide, platinum-black or oxidized iridium. Due to the layer 60 being porous there is no longer any need for the main electrode, i.e. the metal core 40, to also be porous as in conventional electrodes. The conductive layer 60 may either totally cover the piezoelectric material 50 as in FIG. 1A or only parts of it as in FIG. 1B (assuming that the remaining part of the piezoelectric material 50 is covered by some other non-conducting biocompatible material 70 such as e.g. silicon rubber). In this way the sensitivity of the piezoelectric electrode 40, 50, 60 can be made different for different geometrical directions. The stimulating electrical current density in the tissue near the electrode can be increased as well as the shape of the mechanical wave front in favor of a lowest possible stimulation threshold. If the piezoelectric material 50 is biocompatible, however, there is no need to cover the remaining part thereof. Moreover, an electrode 10 having a biocompatible piezoelectric material 50 would then function even if the protection layer constituting the conductive layer may be damaged.

According to another embodiment of the invention, FIGS. 1C and 1D show a coaxial stimulating and sensing piezoelectric electrode 40, 50, 60. The coaxial piezoelectric electrode 40, 50, 60 is positioned about 1 to 15 cm behind the tip forming an endocardium stimulation electrode 200. This embodiment may e.g. be used in a single lead DDD pacemaker system as disclosed in U.S. Pat. No. 5,476,499. The tip is thereby screwed into the atrial myocardium and a loop descends into the ventricle and makes contact with the ventricular wall. The design of the lead 11 is such that the ring 10 of the lead 11 is in the contact area and the ring 10 includes the coaxial piezoelectric electrode 40, 50, 60. The lead 11 must have two conductors in this case. One conductor 12 is connected to the tip and atrial part of the DDD pacemaker. The other conductor 13 is connected to the piezoelectric electrode 40, 50, 60 and the ventricular circuits of the pacemaker. The block schematics in FIGS. 3, 4 and 5 are thus applicable. The interactions between the atrial and ventricular parts of the DDD pacemaker are well known to a person of skill in pacemaker technology.

FIG. 1E shows a schematic equivalent circuit 45, 60 of the electrode in accordance with an embodiment of the invention, whereby the piezoelectric electrode 40, 50 is characterized by a voltage source Vp and a capacitor Cp. The electrode 10 is further characterized by the tip 60. The conductor 13, 20 electrically connects the electrode to the electronics of the pacemaker.

A stimulation pulse delivered to the electrode 10 and thus to the piezoelectrode 45, will change the thickness of the piezoelectric material during the pulse and two pressure waves will be emitted therefrom, there being one pressure wave for each slope of the stimulation wave. The capacitor Cp of the piezoelectric electrode 40, 50, 60 transmits the electrical stimulation pulse to the heart cells.

FIG. 2 shows a pulse diagram of the detector input signal generated by the electrode in accordance with an embodiment of the invention and including the stimulation pulse, the electrical evoked response A and the electrical signal B corresponding to the mechanical evoked response. Consequently, a successful heart stimulation will be sensed as two electrical signals by the detector 110 shown in FIG. 3. First the muscle cells close to the electrode will immediately after the stimulation pulse generate an electrical signal A related to the trigged ion transport. Then the global heart muscle contraction will exert a mechanical pressure on the piezoelectrode 45 which generates the second electrical signal B. The electrical signal B arrives within a time window C after a certain time D of the electrical signal A. The time interval D depends on the location of the electrode and on the activity of the autonomic nervous system, however, the time interval D is substantially constant for each individual. The time interval D is approximately 5 to 100 ms if the electrode is located in the ventricle. Furthermore, the electrical signal B appears in a relatively narrow time window C, which is approximately 50 ms if the electrode is located in the ventricle.

A control unit 130, e.g. a microprocessor, can analyze the detected electrical signals A and B and how they relate to each other and to the stimulation pulse, so that information regarding the condition of the heart can be obtained. This information can therefore be used as a diagnostic tool for analyzing the condition of the heart.

The control unit 130 may obtain information from the dual sensing detector for analyzing the evoked response signals. It is e.g. often difficult to handle fusion beats in pacemakers embodying an autocapture function. A fusion beat is a cardiac depolarization (atrial or ventricular) resulting from two foci. A pacing stimulation and a spontaneous elicited wave front may both contribute to the electrical activation of that chamber. Another difficulty when analyzing evoked response signals is related to the declining electrode polarization after the stimulation pulse. If the polarization artifact is large, compared to the electrical signal generated by the heart, the control unit 130 may interpret the polarization as a capture. A capture means that (it is assumed) the stimulation resulted in a heart contraction.

Using this electrode, a new possibility for the control unit 130 to verify capture has been created. If the electrical signal B does not fall within the time interval C, the heart contraction is probably not related to the stimulation pulse. If the electrical signal B arrives before the time window C, a fusion beat is present, or the QRS detector sensitivity is set too low, so that the pacemaker does not inhibit the pacing pulse. If the electrical signal B arrives after the time window C, there is a loss of capture followed by a spontaneously emitted heart beat.

If only the electrical signal A is present, the QRS-detector either senses the polarization artifact due to the QRS-detector sensitivity being too high and should be adjusted, i.e. evoked response oversensing, or the patient has a beat with electromechanical dissociation.

By analyzing the morphology, i.e. duration and amplitude, of the electric signal B, information regarding the heart contractility can be obtained. For patients with coronary artery disease, the contractile behavior is changed during angina pectoris. With the electrode according to the invention it is possible for the pacemaker to detect this adverse situation and start therapy. The pacing rate should be reduced until the attack is over. This function is especially important for physiologically rate controlled pacemakers such as those controlled by venous oxygen contents.

Certain patients have a prolonged or varying time between the atrial stimulation A and the atrial evoked electrical response. By letting the control unit 130 start the A-V timer in a two chamber pacing system after the detection of the electrical signal B corresponding to the mechanical evoked response, instead of after the evoked electrical response, these patients will obtain a more stable heart function. The A-V timer is the timer keeping track of the time elapsed between the atrial stimulation A and the ventricular stimulation V.

There are times when the heart in response to a stimulation pulse emits an electrical signal, but does not actually contract (electromechanical dissociation) but the pacemaker detects and interprets the electrical signal as an evoked response. Since the electrode according to the invention registers both electrical and mechanical evoked response, it can distinguish e.g. hemodynamically stable tachycardias at exercise from a pathological situation. Consequently, the electrode according to the invention is suitable for therapy when using an implantable cardiac defibrillator.

FIG. 3 shows the schematic drawing of a heart pacemaker 100 for tissue stimulation. The heart pacemaker 100 has a stimulation pulse generator 120 with an output side connected via a lead 11 to an electrode 10 applied in the ventricle of the heart for delivering stimulation pulses to the heart. Of course, although FIG. 3 shows the electrode 10 to be located in the ventricle, the invention also is useable with the electrode 10 being located in the atrium. The stimulation pulse generator 120 can be activated to deliver a stimulation pulse via a control line, which is connected to a corresponding output of a control unit 130, e.g. a microprocessor. The stimulation pulse generated by the stimulation pulse generator 120 may be any type of stimulation pulse known to the skilled person. The duration of each stimulation pulse as well as the amplitude thereof are set by the control unit 130. In the illustrated preferred embodiment, the control unit 130 has access to a memory 140 wherein a program that execute all functions of the heart pacemaker 100 via the control unit 130 is stored. The pacemaker 100 has a telemetry unit 150 connected to the control unit 130 for programming and for monitoring the functions of the pacemaker 100 and for monitoring parameters acquired therewith on the basis of data exchange with an external programming and monitoring device (not shown).

In order to be able to acquire the reaction of the heart given a stimulation, the pacemaker 100 has a detector unit 110 which has an input side connected via the lead 11 to the electrode 10 for acquiring the heart tissue response signals. This arrangement is simple because only a single electrode 10 is required both for stimulating the heart and for acquiring the reaction thereof. Of course, the electrode according to the invention may be used only as stimulation electrode for stimulating tissue or a measuring electrode for acquiring the evoked response for e.g. operating in the VDD stimulating mode. In such cases either the stimulation generator 120 is programmed not to deliver stimulation pulses or the detector unit 110 not to register any evoked response (not shown).

The control unit 130 further includes circuitry for evaluating the electrical signals received by the detector 10 for making a diagnosis of the condition of the heart depending on e.g. the morphology of the electrical signal B or how the two electrical signals A and B relate to each other, and/or to the stimulation pulse, and possibly for starting a therapy based on the diagnosis.

All of the components of the pacemaker 100 are contained within, or connected to, a housing 101, having a size and shape allowing it to be implanted in a subject.

FIG. 4 shows a schematic circuit diagram of a pacemaker in accordance with a first embodiment of the invention. The stimulation pulse generator includes a charge pump 121, a capacitor $C_1$, e.g. 1 $\mu$F, and a switch S1 which, when closed, charges the capacitor to a voltage of e.g. 20 V. When the stimulation pulse generator 120 rapidly transfers charge to the electrode 10, the thickness of the piezoelectric material 50 changes and pressure waves are emitted to the heart tissue. It is known that mechanical irritation of the endocardium can start a heart contraction, the mechanical stimulation may decrease the threshold for the electrical stimulation or may by itself initiate a heart contraction. Because the piezoelectric electrode 40, 50, 60 functions as a capacitor as well, electrical current is transferred to the tissue when closing the switch S2. Since the capacitance Cp of the piezoelectric material preferably is 10 to 100 nF, a relatively high voltage of about 5 to 25 volt is needed during a very short time of about 10 to 100 $\mu$s for reaching the stimulation threshold. This voltage may be generated inductively or capacitively and then be stored on $C_1$. If a diode $V_D$ is integrated in the electrode as shown in FIG. 4, stimulation pulses with amplitudes and durations used with normal electrodes may be used with the electrode 10 in accordance with the invention (0,6–5 volt at 0,5 ms). The diode may be incorporated in the piezoelectric material 50 or may be a discrete component connected to the conductive materials 40, 60. After a stimulation pulse the switch S3 is closed during for e.g. 5 to 15 ms so that the piezoelectrode 45 is discharged when the next stimulation pulse arrives. A resistor with a very high resistance $R_{LL}$ may be connected across the diode, in order to avoid a build up of a charge on the Piero capacitance. The detector unit 110 comprising a detector 111 and a charge amplifier 112 detects both electric signals A and B corresponding to the electrical and mechanical evoked response respectively registered by the Piero electrode 45.

An alternative embodiment of the schematic circuit diagram of FIG. 4 is shown in FIG. 5. In order to further influence the stimulation threshold, the stimulation pulse generator 120 may generate a stimulation pulse which is chopped with a high frequency of e.g. 10 to 100 kHz. The chopped stimulation frequency may be obtained by opening and closing the switch S2. Due to the chopped stimulation pulse, the Piero sensor generates a series of pressure waves. Since the high frequency improves the electrical transmission through the Piero capacitor Cp, there is no longer any need to have a diode integrated in the electrode as well as the capacitor$_{Cut}$, the capacitor$_{Cut}$ making it possible to avoid a net current which is not zero through the body.

The piezoelectric electrode 10 may be used together with a defibrillation electrode 300, either as two separated electrodes, i.e. two leads, or in combination on a single lead, whereby the piezoelectric electrode is placed at the tip of the lead and the intravascular defibrillation electrode 300 is placed behind the Piero electrode 10 as is shown in FIG. 6.

As shown in FIG. 7, the inventive piezoelectric electrode can be used in a pacemaker for dual chamber pacing. For this purpose, an additional piezoelectrode 10A connected to a lead 11A is implanted in the atrium, the electrode 10A being constructed and operating the same as described above in connection with the piezoelectric electrode 10. The electrode 11 in the dual chamber embodiment of FIG. 7 is connected to a ventricular detector unit 110B, and the lead 11A is connected to an atrial detector unit 110A. The detector units 110A and 110B operate in the same manner as described above in connection with the detector unit 110. Additionally, as is known for dual chamber pacing, the control unit 130 includes an AV timer 131 which begins timing an AV time after an evoked response is detected following a stimulation pulse, or pulses, emitted by the stimulation pulse generator 120.

Although modifications and changes may be suggested by those skilled in the art, it is the intention of the inventors to embody within the patent warranted hereon all changes and modification as reasonably and properly come within the scope of their contribution to the art.

We claim as our invention:

1. A medical electrode comprising a piezoelectric element adapted for implantation in mechanical and electrical contact with body tissue, said piezoelectric element forming means for electrically and mechanically transferring energy between said piezoelectric element and said body tissue in a direction from said piezoelectric element to said tissue.

2. A medical electrode as claimed in claim 1 wherein said piezoelectric element comprises a metal core covered by piezoelectric material, and a conductive layer covering said piezoelectric material.

3. A medical electrode as claimed in claim 2 wherein said piezoelectric material has a capacitance in a range between 10 and 100 nF.

4. A medical electrode as claimed in claim 2 wherein said conductive layer has a high active surface area forming a high double-layer capacitance.

5. A medical electrode as claimed in claim 2 wherein said conductive layer is comprised of biocompatible material.

6. A medical electrode as claimed in claim 2 wherein said conductive layer surface is comprised of porous material.

7. A medical electrode as claimed in claim 1 wherein said piezoelectric element has a generally hemispherical shape.

8. A medically electrode as claimed in claim 2 wherein said piezoelectric element is planar.

9. A medical electrode as claimed in claim 2 wherein said piezoelectric element is planar and wherein said conductive layer partially covers said piezoelectric material, leaving a remainder, and further comprising biocompatible material covering said remainder.

10. A medical electrode as claimed in claim 1 wherein said piezoelectric element has an annular shape.

11. A medical electrode lead comprising:
at least one electrical connector;
a piezoelectric element adapted for implantation in mechanical and electrical contact with body tissue, said piezoelectric element forming transducer means for transferring electrical energy and mechanical energy between said piezoelectric element and said body tissue in a direction from said piezoelectric element to said tissue;
at least one electrical conductor connecting said electrical connector and said piezoelectric element; and
flexible electrical insulation covering said at least one electrical conductor.

12. A medical electrode lead as claimed in claim 11 wherein said piezoelectric element comprises a metal core covered by piezoelectric material, and a conductive layer covering said piezoelectric material.

13. A medical electrode lead as claimed in claim 11 wherein said at least one electrical conductor has an end disposed remote from said electrical connector, and wherein said piezoelectric element comprises a tip electrode disposed at said end.

14. A medical electrode lead as claimed in claim 13 wherein said piezoelectric element has a hemispherical shape.

15. A medical electrode lead as claimed in claim 13 wherein said piezoelectric element is planar.

16. A medical electrode lead as claimed in claim 11 wherein said at least one electrical conductor has an end disposed remote from said electrical connector, and wherein said piezoelectric element comprises a ring electrode, exposed at an exterior of said insulation between said electrical connector and said end.

17. A medical electrode lead as claimed in claim 11 wherein said piezoelectric element forms transducer means for transferring electrical and mechanical energy in each of said first and second directions, and wherein said medical electrode lead comprises a further electrical connector, in addition to said at least one electrical connector, and a further electrical conductor, in addition to said at least one electrical conductor, connecting said further electrical connector to said piezoelectric element.

18. A medical therapy administration device comprising:
a piezoelectric element adapted for implantation in mechanical and electrical contact with body tissue, said piezoelectric element forming transducer means for transferring electrical energy and mechanical energy between said piezoelectric element and said tissue in a first direction from said piezoelectric element to said tissue and in a second direction from said tissue to said piezoelectric element;
at least one electrical conductor having a first end connected to said piezoelectric element;
electrical insulation surrounding said at least one electrical conductor and adapting said at least on electrical conductor for implantation in a subject;
at least one electrical connector disposed at a second end of said electrical conductor, opposite from said first end;
pulse generator means for emitting electrical stimulation pulses;
detector means for receiving and analyzing signals from said body tissue;
switching means for selectively connecting said pulse generator means and said detector means to said at least one electrical connector for transmitting said pulses to said piezoelectric element and for receiving said signals from said body tissue from said piezoelectric element; and
a housing adapted for implantation in a subject containing said pulse generating means and said detector means.

19. A device as claimed in claim 18 wherein said pulse generator means comprises means for generating chopped stimulation pulses.

20. A device as claimed in claim 19 wherein said pulse generator means comprises means for generating chopped stimulation pulses at a frequency between 10 and 100 kHz.

21. A device as claimed in claim 18 wherein said detector means comprises means for identifying an evoked electrical and mechanical response of said body tissue following stimulation of said body tissue by a stimulation pulse emitted by said pulse generator means.

22. A device as claimed in claim 21 wherein said detector means comprises means for identifying whether said evoked mechanical response arrives before a predetermined time in a window after admission of said stimulation pulse for detecting fusion beats.

23. A device as claimed in claim 18 wherein said detector means comprises means for analyzing heart contractility by determining a morphology of a signal corresponding to mechanical energy received by said piezoelectric element from said tissue.

24. A device as claimed in claim 18 for dual chamber pacing, comprising control means, contained in said housing, for controlling said pulse generator means dependent on an atrial signal from said detector means for dual-chamber pacing, said control means having an A-V timer which begins timing an A-V time after said detector means detects a mechanical evoked response, via piezoelectric element, following a stimulation pulse emitted by said pulse generator means.

25. A device as claimed in claim 18 further comprising control means, contained in said housing, connected to said pulse generator means and to said detector means, for detecting electromechanical dissociation by determining if said detector means does not identify both an electrical and a mechanical evoked response, via said piezoelectric element, following admission of a stimulation pulse by said pulse generator means.

* * * * *